United States Patent
Li et al.

(10) Patent No.: US 11,680,106 B2
(45) Date of Patent: Jun. 20, 2023

(54) BISPECIFIC ANTIGEN-BINDING CONSTRUCT AND PREPARATION METHOD AND USE THEREOF

(71) Applicant: ASCLEPIUS (Suzhou) TECHNOLOGY COMPANY GROUP CO., LTD., Suzhou (CN)

(72) Inventors: Huashun Li, Suzhou (CN); Baoyong Ren, Suzhou (CN)

(73) Assignee: Asclepius (Suzhou) Technology Company Group Co., Ltd., Suzhou (CN)

( * ) Notice: Subject to any disclaimer, the term of this patent is extended or adjusted under 35 U.S.C. 154(b) by 0 days.

(21) Appl. No.: 17/711,121

(22) Filed: Apr. 1, 2022

(65) Prior Publication Data

US 2022/0251238 A1    Aug. 11, 2022

Related U.S. Application Data

(62) Division of application No. 16/300,650, filed as application No. PCT/CN2017/083961 on May 11, 2017, now Pat. No. 11,339,225.

(51) Int. Cl.
*C07K 16/30* (2006.01)
*A61P 35/00* (2006.01)
*C07K 16/28* (2006.01)
*C12N 15/63* (2006.01)

(52) U.S. Cl.
CPC .......... *C07K 16/3015* (2013.01); *A61P 35/00* (2018.01); *C07K 16/2809* (2013.01); *C07K 16/3023* (2013.01); *C07K 2317/31* (2013.01); *C07K 2317/56* (2013.01); *C12N 15/63* (2013.01)

(58) Field of Classification Search
CPC ............ C07K 16/3015; C07K 16/2809; C07K 16/3023; C07K 2317/31; C07K 2317/56; C07K 14/4703; C07K 2317/622; C07K 2317/73; C07K 2319/33; C07K 16/2803; C07K 16/30; A61P 35/00; C12N 15/63; A61K 2039/505
See application file for complete search history.

(56) References Cited

U.S. PATENT DOCUMENTS

2015/0291694 A1*  10/2015  Aburatani ............. A61P 1/16
                                                 424/174.1
2017/0081385 A1     3/2017  Herrin et al.

FOREIGN PATENT DOCUMENTS

| CN | 1795208 A | 6/2006 |
| CN | 101014860 A | 8/2007 |
| CN | 102958942 A | 3/2013 |
| CN | 104487587 A | 4/2015 |
| CN | 104774268 A | 7/2015 |
| CN | 106589129 A | 4/2017 |
| WO | WO 2013/158856 A2 * | 10/2013 | ............. C12P 21/06 |
| WO | WO 2015/095895 A1 | 6/2015 |
| WO | WO 2015/143199 A1 | 9/2015 |

OTHER PUBLICATIONS

Murphy C, Stack E, Krivelo S, Breheny M, Ma H, O'Kennedy R. Enhancing recombinant antibody performance by optimally engineering its format. J Immunol Methods. Dec. 2018;463:127-133. (Year: 2018).*
Leninger M, Sae Her A, Traaseth NJ. Inducing conformational preference of the membrane protein transporter EmrE through conservative mutations. Elife. Oct. 22, 2019;8:e48909. doi: 10.7554/eLife.48909. PMID: 31637997; PMCID: PMC6805155. (Year: 2019).*
Bowie et al., "Deciphering the message in protein sequences: tolerance to amino acid substitutions," Science, 247(4948):1306-1310 (1990).
Burgess et al., "Possible disassociation of the heparin-binding and mitogenic activities of heparin-binding (acidic fibroblast) growth factor-1 from its receptor-binding activities by site-directed mutagenesis of a single lysine residue," J Cell Biol, 111(5):2129-2138 (1990).
Colman, "Effects of amino acid sequence changes on antibody-antigen interactions," Research in Immunology, 145:33-36 (1994).
Howitt et al., "Binding site for Robo receptors revealed by dissection of the leucine-rich repeat region of Slit," EMBO J, 23(22):4406-4412 (2004).
International Search Report for International Application No. PCT/CN2017/083961, dated Aug. 2, 2017.
Leninger et al., "Inducing conformational preference of the membrane protein transporter EmrE through conservative mutations," eLife, 8:48909 (2019).
Morlot et al., "Structural insights into the Slit-Robo complex," Proc Natl Acad Sci U S A, 104(38):14923-14928 (2007).

(Continued)

*Primary Examiner* — Hong Sang
*Assistant Examiner* — Sung Min Yoon
(74) *Attorney, Agent, or Firm* — Finnegan, Henderson, Farabow, Garrett & Dunner, LLP

(57) ABSTRACT

Disclosed are a bispecific antigen-binding construct and the preparation method and use thereof, wherein the construct comprises a first antigen binding unit and a second antigen binding unit, the first antigen binding unit is a single chain variable region antibody fragment ScFV which specifically binds to the surface antigen of immune cells, and the second antigen binding unit is a Slit2D2 protein fragment which specifically binds to the surface antigen Robo1 of tumour cells. That is to say, the construct can bind to the surface antigen of immune cells and the surface Robo1 molecule of tumour cells at the same time, so that as the distance between tumour cells and immune cells get smaller, the quiescent immune cells are effectively activated, and the effect of killing and wounding tumours is produced. The construct has advantages of small molecular weight and good tissue penetrability, has significant killing and wounding effects on the tumour cells which express a large amount of Robo1, and can be used in the development of anti-tumour drugs.

5 Claims, 6 Drawing Sheets

Specification includes a Sequence Listing.

(56) References Cited

OTHER PUBLICATIONS

Murphy et al., "Enhancing recombinant antibody performance by optimally engineering its format," J Immunol Methods, 463:127-133 (2018).
Ngo et al., "The Protein Folding Problem and Tertiary Structure Prediction," pp. 433 and 492-495 (1994).
Rudikoff et al., "Single amino acid substitution altering antigen-binding specificity," Proc Natl Acad Sci USA, 79(6):1979-1983 (1982).
Wang et al., "Induction of tumor angiogenesis by Slit-Robo signaling and inhibition of cancer growth by blocking Robo activity," Cancer Cell, 4(1):19-29 (2003).
Written Opinion of the International Searching Authority for International Application No. PCT/CN2017/083961, dated Aug. 2, 2017.

\* cited by examiner

BISPECIFIC ANTIGEN-BINDING CONSTRUCT AND PREPARATION METHOD AND USE THEREOF

This application is a continuation of U.S. application Ser. No. 16/300,650, filed Nov. 12, 2018, which is a national stage filing under 35 U.S.C. § 371 of International Application No. PCT/CN2017/083961, filed on May 11, 2017, which claims the benefit of the filing date of Chinese Patent Application No. 201610316117.X, filed on May 12, 2016, each of which is incorporated herein by reference.

REFERENCE TO AN ELECTRONIC SEQUENCE LISTING

The contents of the electronic sequence listing are herein incorporated by reference in their entirety.

FIELD OF THE INVENTION

The invention relates to the technical field of immunology, in particular to a bispecific antigen binding construct and a preparation method and application thereof.

BACKGROUND OF THE INVENTION

Robo is a transmembrane receptor protein that crosses the membrane once. Four Robo genes have been cloned from mammals. From the perspective of species evolution, the extracellular portions of Robo1, 2, 3 are highly conserved from *Drosophila* to humans, all consisting of five Ig-like functional regions and three Fibronectin III type repeats. Robos all have a very short transmembrane region and a longer intracellular region; based on the sequence conservation, the intracellular region is divided into four smaller regions, which are individually named as CC0, CC1, CC2, and CC3. The extracellular IgG domains of Robos are thought to be necessary for binding to ligand Slit, and the longer intracellular domain interacts with some important signaling molecules to participate in the signal transduction downstream of Slit/Robo, thereby completing the transmission of the stimulation signal from the exterior of the cell to the internal cytoskeleton. By now the structural analysis of the protein in the interaction region between Slit2 and Robo has been completed, and it is found that the second domain D2 of Slit2 binds to Ig1 of Robo1, and then initiates the signal transduction.

Histopathological examination showed that Robo1 is overexpressed in various types of cancers, such as hepatocellular carcinoma, breast cancer, colon cancer, pancreatic cancer, prostate cancer, glioma, and the like. It was found that Robo1 is abundantly expressed in liver cancer, whereas only a small amount is expressed in normal tissues, and 84.7% of liver cancer tissue samples showed positive expression; the cancerous tissues of 80% of the colon cancer patients had high expression level of Robo1 mRNA, and in 45% of the patients, the expression levels were 4 times over those in normal tissues, in 15% of patients, the expression levels were 12 times over those in normal tissues. Therefore, Robo1 can be regarded as a new tumor associated antigen, and is a potential target for treatment and diagnosis.

The differentiation cluster 3 (CD3) molecule only exists on the surface of T cells, and often binds tightly to T cell receptor (TCR) to form a TCR-CD3 complex, which has the functions of T cell activation signal transduction and stabilizing TCR structure.

The present invention provides a bispecific antigen binding construct with antigen binding sites capable of respectively binding to CD3 and Robo1, and said construct effectively activates resting T cells, thereby achieving the purpose of killing diseased cells.

SUMMARY OF THE INVENTION

One purpose of the present invention is to provide a bispecific antigen binding construct, which comprises a first antigen binding unit and a second antigen binding unit; the first antigen binding unit is an antibody or antibody fragment that specifically binds to an immune cell surface antigen (for example, a single-chain variable fragment (ScFV, also referred to as a single-chain antibody)); the second antigen-binding unit is Slit2 or a fragment thereof (for example, a Slit2D2 fragment) that specifically binds to a tumor cell surface antigen Robo1.

In one embodiment of the present invention, the Slit2D2 fragment has an amino acid sequence that shares at least 80%, 90%, 95%, 96%, 97%, 98%, 99% or 100% sequence identity with SEQ ID NO:1;

In a preferred embodiment of the present invention, the Slit2D2 fragment has an amino acid sequence as shown in SEQ ID NO: 1.

Preferably, the immune cell is selected from a group consisting of a T cell, an NKT cell, and a CIK cell; more preferably a T cell;

Preferably, the first antigen binding unit specifically binds to immune cell surface antigen CD3;

Preferably, the ScFV comprises a heavy chain variable region (VH) and a light chain variable region (VL); in the ScFV, the VH is linked to the N-terminal domain of the VL via its C-terminal domain, or the VH is linked to the C-terminal domain of the VL via its N-terminal domain; the linkage may be a direct linkage without any intermediate linker peptide, i.e., the linkage is formed with mere peptide bond; or the linkage is formed by a linker peptide; preferably, the linkage is formed by a linker peptide that is a polypeptide having 1-20 amino acids, more preferably 10-16 amino acids, further preferably 14 amino acids;

In one embodiment of the invention, the VH comprises an amino acid sequence that shares 80%, 90%, 95%, 96%, 97%, 98%, 99% or 100% sequence identity with SEQ ID NO:2;

In one preferred embodiment of the invention, the VH comprises an amino acid sequence as shown in SEQ ID NO: 2;

In one embodiment of the invention, the VL comprises an amino acid sequence that shares 80%, 90%, 95%, 96%, 97%, 98%, 99% or 100% sequence identity with SEQ ID NO: 3;

In one preferred embodiment of the invention, the VL comprises an amino acid sequence as shown in SEQ ID NO: 3;

In one embodiment of the invention, the ScFV comprises an amino acid sequence that shares 80%, 90%, 95%, 96%, 97%, 98%, 99% or 100% sequence identity with SEQ ID NO: 4;

In one preferred embodiment of the invention, the ScFV comprises an amino acid sequence as shown in SEQ ID NO: 4;

In another embodiment of the invention, the ScFV comprises an amino acid sequence that shares 80%, 90%, 95%, 96%, 97%, 98%, 99% or 100% sequence identity with SEQ ID NO:5;

In one preferred embodiment of the invention, the ScFV comprises an amino acid sequence shown as SEQ ID NO: 5;

Preferably, in the construct, the SlitD2 is linked to the N-terminal domain of the ScFV via its C-terminal domain or the SlitD2 is linked to the C-terminal domain of the ScFV via its N-terminal domain; the linkage may be a direct linkage without any intermediate linker peptide, i.e., the linkage is formed with mere peptide bond; or the linkage is formed by a linker peptide; preferably, the linkage is formed by an interconnecting peptide that is a polypeptide having 1-10 amino acids, more preferably 3-7 amino acids, further preferably 5 amino acids;

In one embodiment of the present invention, the construct is made as: VH-VL-Slit2D2, VL-VH-Slit2D2, Slit2D2-VH-VL, or Slit2D2-VL-VH, wherein the"–" indicates a connecting bond or a linker peptide.

In one preferred embodiment of the invention, the construct comprises an amino acid sequence that shares 80%, 90%, 95%, 96%, 97%, 98%, 99% or 100% sequence identity with SEQ ID NO: 6.

In one more preferred embodiment of the invention, the construct comprises an amino acid sequence as shown in SEQ ID NO: 6.

In one preferred embodiment of the invention, the construct comprises an amino acid sequence that shares 80%, 90%, 95%, 96%, 97%, 98%, 99% or 100% sequence identity with SEQ ID NO:7.

In one more preferred embodiment of the invention, the construct comprises an amino acid sequence as shown in SEQ ID NO: 7.

In one preferred embodiment of the invention, the construct comprises an amino acid sequence that shares 80%, 90%, 95%, 96%, 97%, 98%, 99% or 100% sequence identity with SEQ ID NO:8.

In one more preferred embodiment of the invention, the construct comprises an amino acid sequence as shown in SEQ ID NO: 8.

In one preferred embodiment of the invention, the construct comprises an amino acid sequence that shares 80%, 90%, 95%, 96%, 97%, 98%, 99% or 100% sequence identity with SEQ ID NO:9.

In one more preferred embodiment of the invention, the construct comprises an amino acid sequence as shown in SEQ ID NO: 9.

In one embodiment of the invention, the Slit2D2 fragment, ScFV and bispecific antigen binding construct of the invention further contain variants thereof. Illustratively, the variant may contain or consist of an amino acid sequence which has been obtained by substituting, deleting, inserting, or adding one or several amino acids on the specific amino acid sequence of the present invention or the parent sequence thereof, while retaining the activity before the substitution, deletion, insertion or addition. For example, the variant of the Slit2D2 fragment may comprise or consist of an amino acid sequence derived from substitution, deletion, insertion or addition of one or several amino acids in SEQ ID NO: 1, while retaining the activity before the substitution, deletion, insertion or addition; preferably, the activity refers to specific binding to the tumor cell surface antigen Robo1.

Illustratively, the variant of the ScFV may contain or consist of an amino acid sequence derived from substitution, deletion, insertion or addition of one or several amino acids in SEQ ID NO: 4 or 5, while retaining the activity before substitution, deletion, insertion or addition, Preferably, the activity refers to the specific binding to the immune cell surface CD3 molecules and activate immune cells (e.g., T cells, NKT cells, and CIK cells).

Illustratively, the variant of the bispecific antigen binding construct may contain or consist of an amino acid sequence derived from substitution, deletion, insertion or addition of one or several amino acids in SEQ ID NO: 6, 7, 8 or 9, while retaining the activity before substitution, deletion, insertion or addition; preferably, the activity refers to cytotoxicity on tumor cells (eg, breast cancer cells, liver cancer cells).

The substitution, deletion, insertion or addition of one or several amino acids in the amino acid sequence of the present invention refers to substitution, deletion, insertion or addition of one or several amino acid sequences (e.g. 2, 3, 4, 5, 6, 7, 8, or 9) at any position in the sequence, and two or more of the substitutions, deletions, insertions, and additions may happen concurrently.

The substitution, deletion, insertion or addition of one or several amino acids in the amino acid sequence described in the present invention can be made by site-directed mutagenesis method described in "Molecular Cloning $3^{rd}$ version" and "Current Protocols in Molecular Biology" (Modern Molecular Biology Practice).

The invention also provides a nucleotide encoding the aforesaid construct protein.

In one preferred embodiment of the invention, the encoding nucleotide comprises a sequence shown as SEQ ID NO: 10 or the complement sequence thereof.

In one preferred embodiment of the invention, the encoding nucleotide of the invention comprises its variants, for example, a polynucleotide hybridizing under stringent conditions with the nucleotide sequence as shown in SEQ NO: 10 or with a sequence complementary to SEQ ID NO:10, and encoding an amino acid sequence having cytotoxicity against tumor cells (for example, breast cancer cells, liver cancer cells); or The "stringent conditions" described herewith may be any of low stringency conditions, medium stringency conditions, and high stringency conditions, preferably high stringency conditions. Illustratively, the "low stringency conditions" may be 30° C., 5×SSC, 5×Denhardt solution, 0.5% SDS, 52% formamide; the "medium stringent conditions" may be 40° C., 5×SSC, 5×Denhardt solution, 0.5% SDS, 52% formamide conditions; the"high stringency conditions" may be 50° C., 5×SSC, 5×Denhardt's solution, 0.5% SDS, 52% formamide. A person skilled in the art should understand that polynucleotides with higher homology would be obtained under higher temperature. In addition, in order to achieve the desired level of stringency, a person skilled in the art is able to manipulate a comprehensive effect of a plurality of factors which affect the stringency of hybridization, including probe concentration, probe length, ionic strength, length of time, salt concentration, etc.

The invention also provides a vector comprising the aforesaid encoding nucleotide.

In one embodiment of the invention, the vector may be a recombinant plasmid, recombinant cell, recombinant strain, or a recombinant virus containing the aforesaid nucleotide encoding the construct protein.

The construct of the present invention can be artificially synthesized, or it may be obtained by synthesizing the encoding gene thereof first, and then obtaining the construct by biological expression.

The invention also provides a method of preparing the aforesaid construct comprising the following steps:
 (1) Constructing a recombinant vector;
 (2) Preparing and fermenting the transformant;
 (3) Isolating and purifying the construct protein;
 Optionally. (4) identifying the construct protein.

The aforesaid step (1) comprises the following specific steps:

Obtaining the gene fragment encoding the construct protein by total gene synthesis, and then gene fragment is used as a template to obtain PCR products by PCR amplification. Then the above product is purified and recovered, and then cloned into a vector plasmid. The resulted recombinant vector is transformed into a first host cell, which is in turn inoculated to a solid medium containing ampicillin (AMP) for propagation, positive clone screening, confirming of the successful construction of the vector by sequencing, and strains preserving;

The vector plasmid is a pCDNA plasmid, preferably pCDNA4.3;

The first host cell includes but is not limited to *E. coli* strain, preferably TOP10 strain.

The step (2) comprises the following specific steps:

Extracting the recombinant vector from the first host cell;

Culturing the second host cell, and transfecting the extracted recombinant vector when the cell density reaches $2.5 \times 10^6$ cells/ml. The second host cell successfully transfected with the target gene is defined as a transformant. The transformant is screened and fermented, and then supernatant is collected after 5 days.

The second host cell includes but is not limited to ExpiCHO cell.

The step (3) comprises the following specific steps:

The supernatant of the culture medium is collected in step (2), and then centrifuged at a high speed and then the construct protein is isolated and purified.

The purification includes but is not limited to the purification of protein by ion exchange chromatography.

The step (4) comprises the following specific steps:

Identifying the molecular weight and purity of the obtained fusion protein.

The molecular weight of said fusion protein can be identified by general protein biochemical means including but not limited to SDS-PAGE. Western blotting and MS, etc.

The purity of said fusion protein is detected by SEC-HPLC.

The invention also provides a pharmaceutical composition comprising the aforesaid bispecific antigen binding construct, and a pharmaceutically acceptable adjuvant.

The pharmaceutical compositions of the invention can be tablets (including sugar-coated tablets, film-coated tablets, sublingual tablets, orally disintegrating tablets, oral tablets, etc.), pills, powder, granules, capsules (including soft capsules, microcapsules), pastilles, syrups, liquids, emulsions, suspensions, controlled release formulations (e.g., instantaneous release formulations, sustained-release formulations, sustained-release microcapsules), aerosols, films (e.g., oral disintegrating films, oral mucosa adhesive films), injections (e.g., subcutaneous injections, intravenous injections, intramuscular injections, intraperitoneal injections), intravenous infusions, transdermal absorption formulations, ointments, lotions, adhesion agents, suppositories (e.g., rectal suppositories, vaginal suppositories), pillers, nasal preparations, lung preparations (inhalations), eye drops, etc., oral or parenteral formulations (e.g., intravenous, intramuscular, subcutaneous, organs, intranasal, intradermal, drip, brain, rectum and other forms of administration to the vicinity tumor and directly to the lesion place). Preferably, the said pharmaceutical composition is an injection agent.

The pharmaceutically acceptable adjuvant in the present invention is preferably a pharmaceutically acceptable injectable adjuvant such as isotonic and sterile salt solution (sodium dihydrogen phosphate, disodium hydrogen phosphate, sodium chloride, potassium chloride, calcium chloride, magnesium chloride, etc., or mixtures of the aforesaid salts), or injectable solutes formed by dried e.g., freeze-dried composition suitably dissolving in sterile water or saline.

The invention also provides the use of the aforesaid bispecific antigen binding construct in the preparation of antitumor drugs.

The invention also provides the use of the above bispecific antigen binding construct in antitumor drugs screening and pharmacology or clinical efficacy evaluation of antitumor drugs.

Preferably, the tumor is a tumor with high expression of Robo1 and related diseases, and the high expression described herein means that the expression level of Robo1 in the tumor cell is higher than that in a normal cell.

In one embodiment of the invention, the tumor disease is liver cancer or breast cancer.

In the present invention, the term "domain" refers to a region with a specific structure and an independent function in a biological macromolecule. For example, the D2 domain of the Slit2 protein refers to the second domain in the four leucine-rich repeats in the Slit2 protein.

The bispecific antigen binding construct provided by the invention can simultaneously bind the surface antigen of immune cells and Robo1 molecules on the surface of tumor cells, in particular, CD3 molecules on the surface of immune cells and Robo1 molecules on the surface of tumor cells, thereby pulling the tumor cells and the immune cells towards each other, and effectively activating the resting immune cells, especially T cells, thereby achieving the tumor-killing effect. Compared with traditional antibodies, the construct has the advantages of lower molecular weight and better tissue penetration capacity, and it possesses a significant killing effect on tumor cells with high Robo1 expression. Therefore, the construct can be used for the development of anti-tumor drugs. Experiments have shown that the bispecific antigen binding constructs of the present invention VH-VL-Slit2D2, LV-VH-Slit2D2, Slit2D2-VL-VH and Slit2D2-VH-VL all show high cytotoxicity against breast cancer cells MDA-MB-231, liver cancer cells SMCC7721 and MHCC97H.

DETAILED DESCRIPTION OF THE INVENTION

The technical solutions in the embodiments of the present invention are clearly and completely described in the following context with reference to the drawings in the embodiments of the present invention. It is obvious that the described embodiments are only a part of the embodiments of the present invention, and not all of the embodiments. Based on the embodiments of the present invention, all other embodiments obtained by a person skilled in the art without any creative work are within the scope of the protection of the present invention.

Example 1: Preparation of the Bispecific Antigen Binding Construct Slit2D2-ScFV

Figure 1:
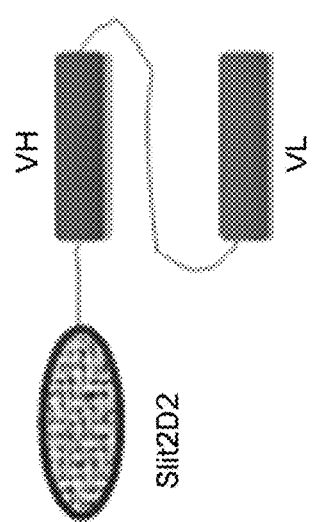
FIG. 1 illustrates a construction scheme of the bispecific antigen binding construct of the invention.

The bispecific antigen binding construct prepared in this example is Slit2D2-VH-VL, and its construction scheme is as shown in FIG. 1.

1. Protein Expression 1.1 Experimental Materials:

Cell line: ExpiCHO-S™ cells (Gibco Catalog No. A29127);

Transfection kit: ExpiFectamine™ CHO Transfection Kit (Gibco Catalog No. A29129) OptiPRO™ SFM (Gibco Catalog No. 12309-050);

Culturing Medium: ExpiCHO™ Expression Medium (Gibco Catalog No. A29100-01);

pCDNA3.4 plasmid vector (Invitron).

Figure 2:
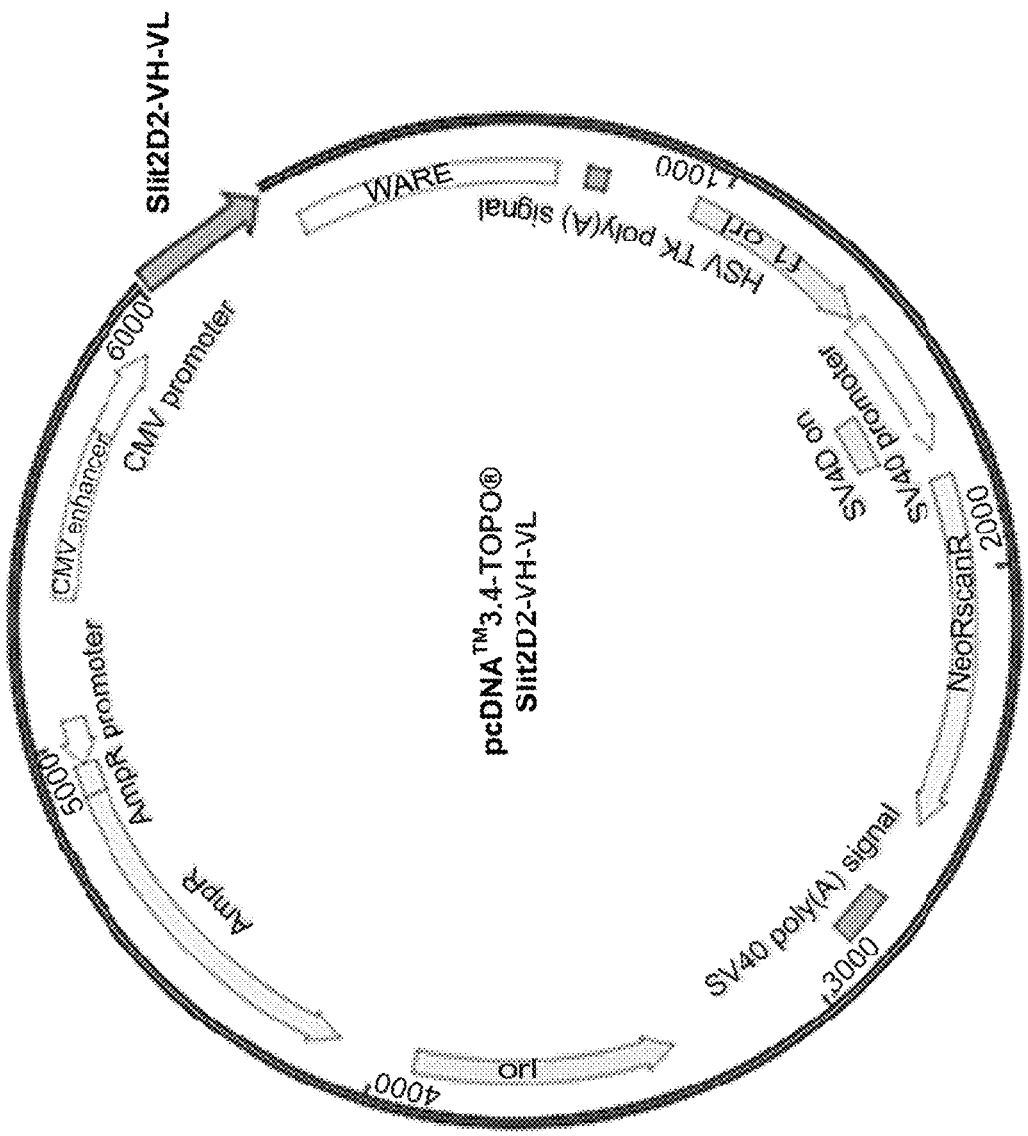
FIG. 2 illustrates an expression vector map of the bispecific antigen binding construct of the present invention.

1.2 Experiment Procedure:

According to the designed Slit2D2-ScFV gene sequence (as shown in SEQ ID NO: 10), the Slit2D2-VH-VL gene fragment was obtained by total gene synthesis, and then PCR product was obtained by PCR amplifying by the Slit2D2-VH-VL gene fragment as a template. The aforesaid product was purified and recovered with a gel recovery kit. According to the theory of T-A cloning, the PCR product was cloned into a pCDNA3.4 vector. The recombinant plasmid map is as shown in FIG. 2. The recombinant plasmid was transformed into E. coli TOP10, and then it was screened with ampicillin. The positive clones were picked and the completion of the construction of the vector was confirmed by sequencing. Plasmid DNA was extracted by using endo-free DNAextraction kit, which was used for the transfection of ExpiCHO-S™ cells. The ExpiCHO-S™ cells were cultured by shaking at 37° C. in an incubator containing 8% $CO_2$. The plasmid DNA was transfected into the ExpiCHO-S™ cells when the density reached $2.5\times10^6$ cells/ml. The transfected ExpiCHO-S™ cells were cultured in the ExpiCHO™ Expression Medium, and the supernatant of the culturing fluid was collected 5 days after transfection and then centrifuged at a high speed. The supernatant was kept for subsequent purification.

2. Protein Purification 2.1 Experimental Instruments and Materials:

AKTA protein purification system;

Binding Buffer: 20 mM phosphate, 0.5 M NaCl, 20 mM imidazole, adjusted to pH 7.4;

Elution Buffer: 20 mM phosphate, 0.5 M NaCl, 500 mM imidazole, adjusted to pH 7.4; deionized water;

20% Ethanol solution.

2.2 Experiment Procedure:

(1) Starting the AKTA device, and connecting a His column to the AKTA;

(2) Washing the His column with 3-5 column volumes of deionized water;

(3) Equilibrating the His column with 5 column volumes of the Binding Buffer;

(4) The filtered cell supernatant was taken out and flowed through the His column in turn;

(5) Washing off the protein impurities with the Binding Buffer until the absorbance approaches zero at UV280;

(6) Eluting the protein of interest using the Elution Buffer, and starting collecting the eluent while absorbance was greater than 400 at UV280;

(7) Dialyzing the collected protein eluent with PBS at 4° C., and the dialyzed protein was stored at −80° C.;

(8) After the collection of protein, washing the His column using 10 column volumes of Binding Buffer;

(9) Washing the His column using 10 column volumes of deionized water;

(10) Washing the His column using 10 column volumes of 20% ethanol, and the His column was placed in 20% ethanol and stored at 4° C.;

(11) Dialyzing the collected protein eluent with a dialysis bag to remove the salt ions, and the eluent is converted into a PBS solution for preserving the protein.

Note: a. Use a 0.45 μm filtering membrane to filter all the reagents for use in the purification process.

b. During the purification process, it is prohibited to allow air to enter the His column.

c. The entire process should be performed on ice to prevent protein inactivation.

2.3 Experimental Result

Figure 3:
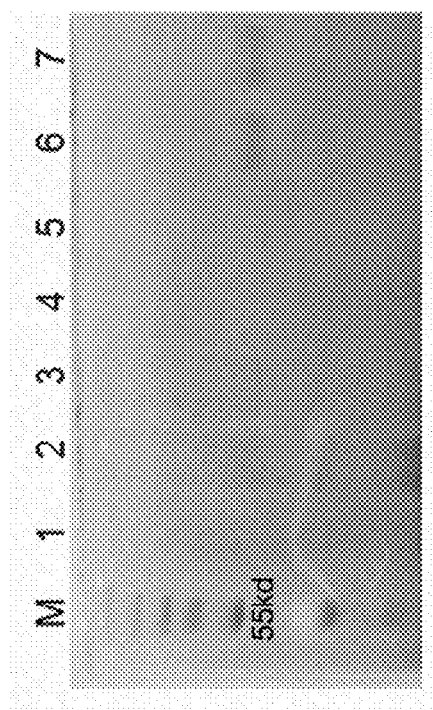
FIG. 3 illustrates a SDS-PAGE electropherogram of the bispecific antigen binding construct protein in Example 1, wherein M is the marker lane, and 6 and 7 are the lanes of the bispecific antigen binding construct protein.

The target protein was obtained by the aforesaid purification procedure, and its SDS-PAGE electrophores is as shown in FIG. 3. As shown in FIG. 3, the molecular weight of the target protein was about 55 KD with extremely high purity. No protein impurity was detected, and it was indicated that the recombinant expression vector of Slit2D2-VH-VL had been successfully constructed, and the expression of Slit2D2-VH-VL in the host cell had been achieved.

Example 2 Tumor Killing Test for Detecting the Drug Activity

The killing activity of the drug on tumor cells was determined by lactate dehydrogenase (LDH) releasing method.

1.1 Experimental Materials:

Test kit: CytoTox 96@ Non-Radioactive Cytotoxicity Assay kit (promega);

Kit components: 5 vials of Substrate Mix, 60 ml Assay Buffer, 25 μl LDH Positive Control, 5 ml Lysis Solution (10×), 65 ml Stop Solution;

Target cells: breast cancer cells MDA-MB-231, liver cancer cells SMCC7721, PBMC;

Drug: bispecific antigen binding construct protein Slit2D2-VH-VL (obtained from the preparing and purifying in Example 1);

Medium: DMEM (10% FBS, 5% double antibody) (Gibco), T cell medium (Gibco);

Reagent preparation: Assay Buffer was incubated at 37° C. 12 ml Assay Buffer is taken into a Substrate Mix bottle to prepare the CytoTox96® Reagent.

1.2 Experiment Procedure:

(1) Target cells (MDA-MB-231/SMCC7721) is taken and added into a 96-well plate at 100 μl/$4\times10^3$/well;

Effector cells PBMC is taken and added into a 96-well plate at 100 μl/$2\times10^5$/well (i.e., effector-target ratio is 50:1);

The drug was prepared in 3 ladder gradients: 1.2 μg/ml, 0.12 μg/ml, and 0.012 μg/ml;

The Design of LDH release control group (6 replicate wells was set up in each group):

(a) Culture solution control group: pure serum-free 1640 culture solution;

(b) LDH low release group: target cells $4\times10^3$/well;

(c) LDH high release group: target cells 4×10³/well (treated after culturing);

(d) Effector cell control group: PBMC 2×10⁵/well;

(2) Putting the 96-well plate with cells into an incubator set at 37° C. and a volume fraction of 5% $CO_2$ to culture overnight (18-24 hours);

(3) After the culture is ended, adding lysate (Lysis Solution 10×) to the LDH high release group at 1l/O well, and incubating at 37'C for 45-60 min;

(4) Transferring cells of each well to an EP tube, and centrifuging at 1000 rpm for 5 min;

(5) 50 μl of supernatant obtained by the aforesaid centrifugation was taken and added into an ELISA plate and added with 50 μl of CytoTox® Reagent to each well of ELISA plate, and then incubated at room temperature for 30 min;

(6) Adding 50 μl of Stop Solution to each well to terminate the reaction;

(7) Using a microplate reader to detect the absorbance value of the sample obtained in the step (6) at 492 nm.

1.3 Experimental Results:

Calculation formula of killing activity of tumor cells is:

% cytotoxicity=(experimental group−LDH low release group−effector cell control group)/(LDH low release group−LDH low release group)× 100%

Figure 4:
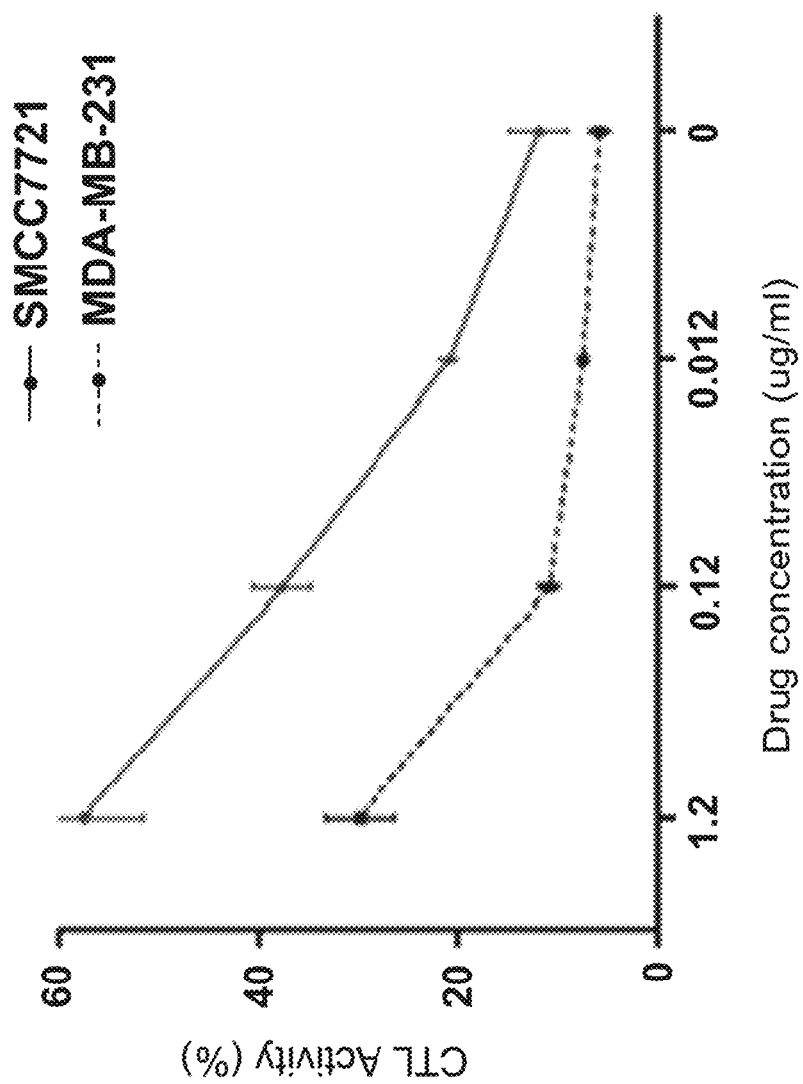
FIG. 4 illustrates a result of tumor killing experiments for detecting the drug activity in Example 2.

The experimental result is as shown in FIG. 4. As shown in FIG. 4, the drug (bispecific antigen binding construct protein Slit2D2-VH-VL prepared and purified in Example 1) show significant killing activity in both liver cancer cell SMCC-7721 and breast cancer cell MDA-MB-231 cells, and the killing activity of the drug was increased with the drug concentration.

Example 3

1.1 Experimental Design

The experiment was divided into three groups: 1. blank control group (a group free from PBMCinoculation), 2. solvent control group, 3. sample group. The design of the experiment is as shown in Table 1.

TABLE 1

Experimental Design

| Groups | Number of animals | Testing sample | Testing sample dosage(mg/kg) | Method of administering | Drug delivery cycle |
|---|---|---|---|---|---|
| 1 | 4 | — | — | — | — |
| 2 | 8 | Solvent control | 0 | i.v | qd × 7 day |
| 3 | 8 | ZD016 | 1 | i.v | qd × 7 day |

Note:
i.v: tail vein administration;
qd: one administering per day;
ZD016: Slit2D2-VH-VL, which was prepared and purified in Example 1.

1.2 Experimental Materials 1.2.1 Experimental Animals: 20 NOD/SCID mice, male, 5-6 weeks (the age at which tumor cell inoculation is carried out, in weeks), weighed 19.3-21.7 g. The mice are purchased from Beijing Huafukang Biotechnology Co., Ltd., and the animal certificate number is 11401300037778. The mice are maintained under SPF level environment.

1.2.2 Experimental Sample: ZD016, packaging specification: 0.65 mg/ml×0.5 ml×3 vials, sealed preservation at −80° C.

1.2.3 Cells: PBMC, packaging specification: 5 ml×1 vial, sealed preservation at −80° C., 9×10⁷ cells are obtained upon recovery, and the cell survival rate is 94.2%.

1.3 Experimental Methods and Steps 1.3.1 Preparation of Test Drug

Solvent control group: PBS, stored at 4° C.;

Sample group: 0.554 ml of ZD016 was taken and added with 3.046 ml of PBS, and the mixture was vortexed evenly to give 3.6 ml of 0.1 mg/ml solution. The solution was filtered and ready for use.

All operations were performed on ice and stored at −80° C.

1.3.2 Cells: MHCC97H cells were cultured in the DMEM medium containing 10% fetal bovine serum. MHCC97H cells in the exponential growth phase were collected, and resuspended in PBS to a suitable concentration and then mixed with the PBMCat 1:1, and then matrigel was added at a same volume for injecting tumors subcutaneously into mice.

1.3.3 Animal Modeling and Grouping: 20 male mice were intraperitoneally injected with CD122 (0.2 mg/mouse) on the day before inoculation, and 5×10⁶MHCC97H+5×10⁶ PBMC cells were inoculated subcutaneously on the right side on the day of inoculation. The animals were randomly grouped in the dosing on the day of inoculation (see Table 1).

1.3.4 Experimental Observation: After tumor inoculation, routine monitoring includes the effects of the tumor growth and the treatment on normal behavior of animals, and Specifically, the contents of which include the activity of the experimental animals, eating and drinking, weight gain or loss (the weight was measured 3 times per week), eyes, coat and other abnormal conditions. The clinical symptoms observed during the experiment were all recorded in the raw data.

The experimental protocols for animal experiments in this experiment were reviewed and approved by Animal Ethics Committee. During the experiment, the animal experiments were all carried out according to the requirements of AAALAC.

1.3.5 Determination of Treatment Based on Experimental Results

Relative tumor inhibition rate TGI (%): TGI=1−T/C (%). T/C % is the relative tumor growth rate, i.e., the percentage of the relative tumor volumes of the treatment group and the control group at a certain time point, wherein T and C are the relative tumor volumes (RTV) of the treatment group and the control group at a certain time point, respectively.

The calculation formula is as follows: T/C %=$T_{RTV}$/$C_{RTV}$*100% ($T_{RTV}$: mean RTV of the treatment group; $C_{RTV}$: mean RTV of the solvent control group; RTV=$V_t$/$V_0$, $V_0$ is tumor volume of the animal at the time of grouping, and $V_t$ is tumor volume of the animal after treatment).

1.3.6 Experimental Termination Point

When a single tumor volume exceeds 3000 mm³ in one single animal, or the average tumor volume exceeds 2000 mm³ in a group of animals, or when the animals were at agonal stage, the single or whole group of animals was euthanized.

In the experiment, on the 25th day after grouped administration (on the 25th day after inoculation), the mean tumor value of the non-PBMC-inoculated group reached 1464 mm³, and the mean tumor value of the solvent control group reached 776 mm³. After the tumor volume was recorded, the mice were euthanized, and then the experiment was terminated. No tissue was collected.

Figure 5:
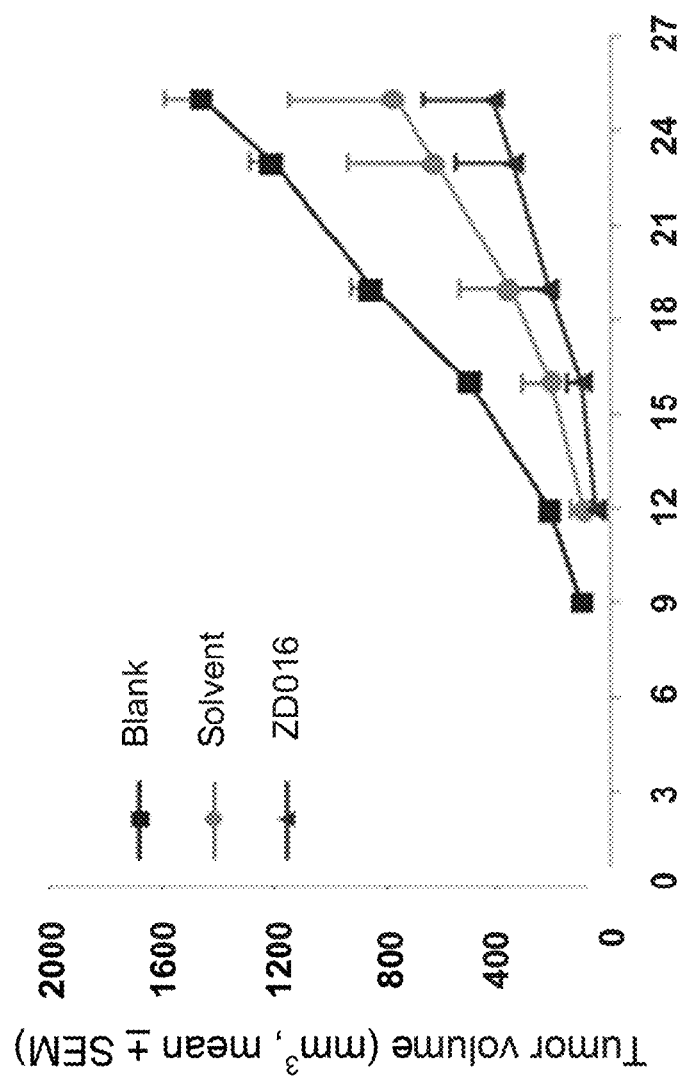
FIG. 5 illustrates a growth change result of the tumor volume of the treatment group and the control group mice of the MHCC97H+PBMC tumor model in Example 3.

1.4 Experimental Result
1.4.1 Result of Anti-tumor Effect of Test Drug ZD016 in the MHCC97H+PBMC Tumor Model The Tumor growth of the treatment group and the control group is as shown in Table 2 and FIG. 5.

The average tumor volume of the completely blank control group (the group free of PBMCinoculation) was 1464 mm$^3$ 25 days after grouped administration, and the average tumor volume of the solvent control group was 776 mm$^3$ 25 days after grouped administration. The average tumor volume of the test group ZD016 (1 mg/kg, qd×7 days) was 421 mm$^3$ 25 days after grouped administration, and the relative tumor inhibition rate TGI (%) was 45.76%.

TABLE 2

TGI and T/C values of each experimental group in the MHCC97H + PBMC tumor model

| Experimental group | 19 days after grouped administration | | | |
|---|---|---|---|---|
| | Tumor volume ($\bar{\chi}$ ± S, mm$^3$) | TGI | T/C(%) | P Vlaue (compared with the control group) |
| The first group: completely blank control group | 1464 ± 127 | — | — | — |
| The second group: solvent control group | 776 ± 375 | — | — | — |
| The third group ZD016(1 mg/kg) | 421 ± 243 | 45.76 | 54.24 | 0.4400 |

1.4.2 Safety Study Results of the Test Drug ZD016 in the MHCC97H+PBMC Tumor Model The test drug ZD016 (1 mg/kg, qd×7 days) treatment group showed no animal death, and no obvious drug toxicity, and said drug was well tolerated during the treatment.

Figure 6:
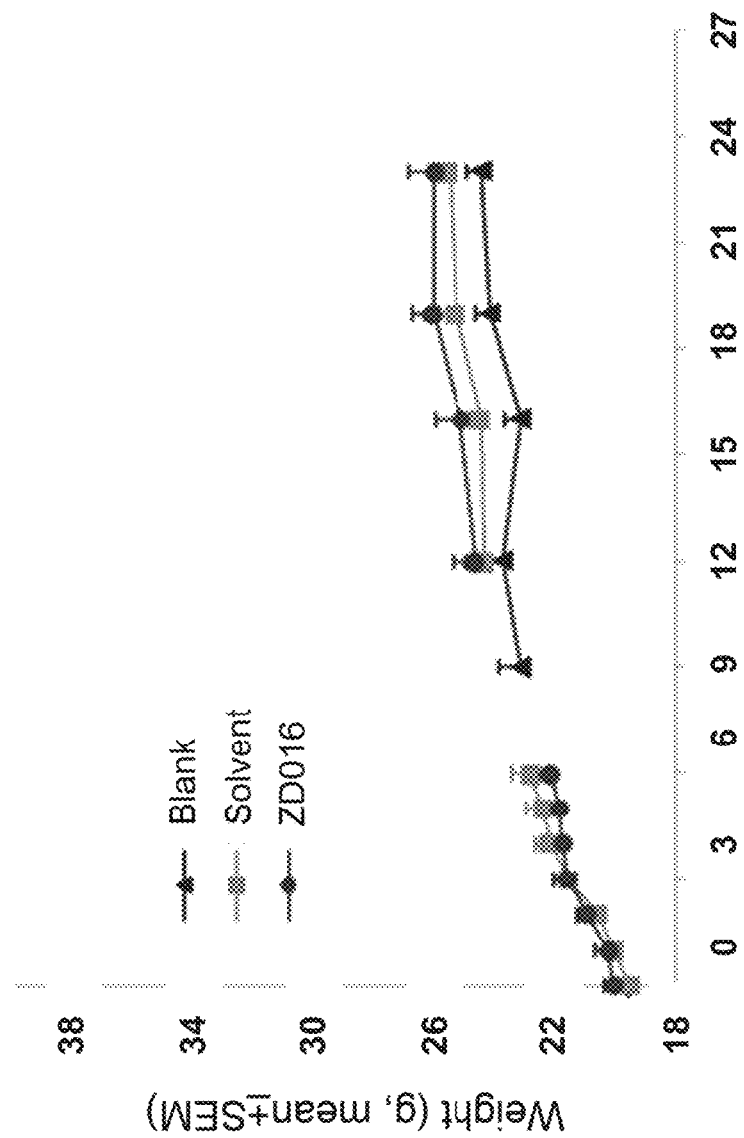
FIG. 6 illustrates the change of body weight of experimental mice over treating time, wherein the mice is from the MHCC97H+PBMC tumor model in Example 3.

The weight changes in the treatment group and the control group upon administration are as shown in FIG. 6.

The above only shows the preferred embodiment of the present invention, and is not intended to limit the scope of the present invention. Any modifications, equivalents, and the like made within the spirit and principles of the present invention should be included in the scope of the present invention.

The invention claimed is:

1. A nucleotide encoding:

a bispecific antigen-binding construct comprising a first antigen-binding unit and a second antigen-binding unit, wherein the first antigen-binding unit is an antibody or an antibody fragment that specifically binds to an immune cell surface antigen CD3; and the second antigen-binding unit is a Slit2 or a Slit2 fragment that specifically binds to a tumor cell surface antigen RoBo1;

wherein the first antigen-binding unit is an antibody or an antibody fragment comprising a VH and a VL of SEQ ID NOs: 2 and 3, respectively; wherein the second antigen-binding unit is a Slit2 or Slit2 fragment that comprises SEQ ID NO: 1; wherein the construct comprises the amino acid sequence SEQ ID NO: 6, SEQ ID NO: 7, SEQ ID NO: 8, or SEQ ID NO: 9.

2. A vector comprising the nucleotide of claim 1.

3. A method of treating a tumor disease by administering:

a bispecific antigen-binding construct comprising a first antigen-binding unit and a second antigen-binding unit, wherein the first-antigen binding unit is an antibody or an antibody fragment that specifically binds to an immune cell surface antigen CD3; the second antigen-binding unit is a Slit2 or a Slit2 fragment that specifically binds to a tumor cell surface antigen RoBo1; wherein the first antigen-binding unit is an antibody or an antibody fragment comprising a VH and a VL of SEQ ID NOs: 2 and 3, respectively; wherein the second antigen-binding unit is a Slit2 or Slit2 fragment that comprises SEQ ID NO: 1; wherein the construct comprises the amino acid sequence SEQ ID NO: 6, SEQ ID NO: 7, SEQ ID NO: 8, or SEQ ID NO: 9.

4. The method of claim 3, wherein the tumor disease is characterized by increased expression of RoBo1 in the tumor cells as compared to normal cells.

5. The method of claim 4, wherein the tumor disease is lung cancer or breast cancer.

\* \* \* \* \*

SEQUENCE LISTING

```
<160> NUMBER OF SEQ ID NOS: 10

<210> SEQ ID NO 1
<211> LENGTH: 209
<212> TYPE: PRT
<213> ORGANISM: Artificial Sequence
<220> FEATURE:
<223> OTHER INFORMATION: SEQ ID NO:1 - Synthetic

<400> SEQUENCE: 1

Leu His Cys Pro Ala Ala Cys Thr Cys Ser Asn Asn Ile Val Asp Cys
1               5                   10                  15

Arg Gly Lys Gly Leu Thr Glu Ile Pro Thr Asn Leu Pro Glu Thr Ile
                20                  25                  30

Thr Glu Ile Arg Leu Glu Gln Asn Thr Ile Lys Val Ile Pro Pro Gly
            35                  40                  45

Ala Phe Ser Pro Tyr Lys Lys Leu Arg Arg Ile Asp Leu Ser Asn Asn
        50                  55                  60

Gln Ile Ser Glu Leu Ala Pro Asp Ala Phe Gln Gly Leu Arg Ser Leu
65                  70                  75                  80

Asn Ser Leu Val Leu Tyr Gly Asn Lys Ile Thr Glu Leu Pro Lys Ser
                85                  90                  95

Leu Phe Glu Gly Leu Phe Ser Leu Gln Leu Leu Leu Leu Asn Ala Asn
                100                 105                 110

Lys Ile Asn Ser Leu Arg Val Asp Ala Phe Gln Asp Leu His Asn Leu
            115                 120                 125

Asn Leu Leu Ser Leu Tyr Asp Asn Lys Leu Gln Thr Ile Ala Lys Gly
        130                 135                 140

Thr Phe Ser Pro Leu Arg Ala Ile Gln Thr Met His Leu Ala Gln Asn
145                 150                 155                 160

Pro Phe Ile Cys Asp Cys His Leu Lys Trp Leu Ala Asp Tyr Leu His
                165                 170                 175
```

```
Thr Asn Pro Ile Glu Thr Ser Gly Ala Arg Cys Thr Ser Pro Arg Arg
            180                 185                 190

Leu Ala Asn Lys Arg Ile Gly Gln Ile Lys Ser Lys Lys Phe Arg Cys
        195                 200                 205

Ser

<210> SEQ ID NO 2
<211> LENGTH: 121
<212> TYPE: PRT
<213> ORGANISM: Artificial Sequence
<220> FEATURE:
<223> OTHER INFORMATION: SEQ ID NO:2 - Synthetic

<400> SEQUENCE: 2

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu
        115                 120

<210> SEQ ID NO 3
<211> LENGTH: 108
<212> TYPE: PRT
<213> ORGANISM: Artificial Sequence
<220> FEATURE:
<223> OTHER INFORMATION: SEQ ID NO:3 - Synthetic

<400> SEQUENCE: 3

Val Asp Asp Ile Gln Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Val Ala Ser Gly Val Pro Tyr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95

Leu Thr Phe Gly Ala Gly Thr Lys Leu Glu Leu Lys
            100                 105

<210> SEQ ID NO 4
<211> LENGTH: 243
<212> TYPE: PRT
<213> ORGANISM: Artificial Sequence
```

<220> FEATURE:
<223> OTHER INFORMATION: SEQ ID NO:4 - Synthetic

<400> SEQUENCE: 4

```
Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
        195                 200                 205

Leu Thr Ile Ser Ser Met Glu Ala Glu Asp Ala Ala Thr Tyr Tyr Cys
    210                 215                 220

Gln Gln Trp Ser Ser Asn Pro Leu Thr Phe Gly Ala Gly Thr Lys Leu
225                 230                 235                 240

Glu Leu Lys
```

<210> SEQ ID NO 5
<211> LENGTH: 243
<212> TYPE: PRT
<213> ORGANISM: Artificial Sequence
<220> FEATURE:
<223> OTHER INFORMATION: SEQ ID NO:5 - Synthetic

<400> SEQUENCE: 5

```
Val Asp Asp Ile Gln Leu Thr Gln Ser Pro Ala Ile Met Ser Ala Ser
1               5                   10                  15

Pro Gly Glu Lys Val Thr Met Thr Cys Arg Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Val Ala Ser Gly Val Pro Tyr Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Tyr Cys Gln Gln Trp Ser Ser Asn Pro
                85                  90                  95
```

```
Leu Thr Phe Gly Ala Gly Thr Lys Leu Glu Leu Lys Gly Gly Ser Gly
                100                 105                 110

Gly Ser Gly Gly Ser Gly Gly Ser Gly Gly Asp Ile Lys Leu Gln Gln
                115                 120                 125

Ser Gly Ala Glu Leu Ala Arg Pro Gly Ala Ser Val Lys Met Ser Cys
            130                 135                 140

Lys Thr Ser Gly Tyr Thr Phe Thr Arg Tyr Thr Met His Trp Val Lys
145                 150                 155                 160

Gln Arg Pro Gly Gln Gly Leu Glu Trp Ile Gly Tyr Ile Asn Pro Ser
                165                 170                 175

Arg Gly Tyr Thr Asn Tyr Asn Gln Lys Phe Lys Asp Lys Ala Thr Leu
                180                 185                 190

Thr Thr Asp Lys Ser Ser Ser Thr Ala Tyr Met Gln Leu Ser Ser Leu
                195                 200                 205

Thr Ser Glu Asp Ser Ala Val Tyr Tyr Cys Ala Arg Tyr Tyr Asp Asp
            210                 215                 220

His Tyr Cys Leu Asp Tyr Trp Gly Gln Gly Thr Thr Leu Thr Val Ser
225                 230                 235                 240

Ser Val Glu

<210> SEQ ID NO 6
<211> LENGTH: 488
<212> TYPE: PRT
<213> ORGANISM: Artificial Sequence
<220> FEATURE:
<223> OTHER INFORMATION: SEQ ID NO:6 - Synthetic

<400> SEQUENCE: 6

Met Glu Thr Asp Thr Leu Leu Leu Trp Val Leu Leu Leu Trp Val Pro
1               5                   10                  15

Gly Ser Thr Gly Gly Gly Gly Ser Asp Ile Lys Leu Gln Gln Ser
                20                  25                  30

Gly Ala Glu Leu Ala Arg Pro Gly Ala Ser Val Lys Met Ser Cys Lys
            35                  40                  45

Thr Ser Gly Tyr Thr Phe Thr Arg Tyr Thr Met His Trp Val Lys Gln
        50                  55                  60

Arg Pro Gly Gln Gly Leu Glu Trp Ile Gly Tyr Ile Asn Pro Ser Arg
65                  70                  75                  80

Gly Tyr Thr Asn Tyr Asn Gln Lys Phe Lys Asp Lys Ala Thr Leu Thr
                85                  90                  95

Thr Asp Lys Ser Ser Ser Thr Ala Tyr Met Gln Leu Ser Ser Leu Thr
            100                 105                 110

Ser Glu Asp Ser Ala Val Tyr Tyr Cys Ala Arg Tyr Tyr Asp Asp His
        115                 120                 125

Tyr Cys Leu Asp Tyr Trp Gly Gln Gly Thr Thr Leu Thr Val Ser Ser
    130                 135                 140

Val Glu Gly Gly Ser Gly Gly Ser Gly Gly Ser Gly Gly Ser Gly Gly
145                 150                 155                 160

Val Asp Asp Ile Gln Leu Thr Gln Ser Pro Ala Ile Met Ser Ala Ser
                165                 170                 175

Pro Gly Glu Lys Val Thr Met Thr Cys Arg Ala Ser Ser Ser Val Ser
            180                 185                 190

Tyr Met Asn Trp Tyr Gln Gln Lys Ser Gly Thr Ser Pro Lys Arg Trp
        195                 200                 205
```

```
Ile Tyr Asp Thr Ser Lys Val Ala Ser Gly Val Pro Tyr Arg Phe Ser
    210                 215                 220
Gly Ser Gly Ser Gly Thr Ser Tyr Ser Leu Thr Ile Ser Ser Met Glu
225                 230                 235                 240
Ala Glu Asp Ala Ala Thr Tyr Tyr Cys Gln Gln Trp Ser Ser Asn Pro
                245                 250                 255
Leu Thr Phe Gly Ala Gly Thr Lys Leu Glu Leu Lys Gly Gly Gly Gly
            260                 265                 270
Ser Leu His Cys Pro Ala Ala Cys Thr Cys Ser Asn Asn Ile Val Asp
        275                 280                 285
Cys Arg Gly Lys Gly Leu Thr Glu Ile Pro Thr Asn Leu Pro Glu Thr
    290                 295                 300
Ile Thr Glu Ile Arg Leu Glu Gln Asn Thr Ile Lys Val Ile Pro Pro
305                 310                 315                 320
Gly Ala Phe Ser Pro Tyr Lys Lys Leu Arg Arg Ile Asp Leu Ser Asn
                325                 330                 335
Asn Gln Ile Ser Glu Leu Ala Pro Asp Ala Phe Gln Gly Leu Arg Ser
            340                 345                 350
Leu Asn Ser Leu Val Leu Tyr Gly Asn Lys Ile Thr Glu Leu Pro Lys
        355                 360                 365
Ser Leu Phe Glu Gly Leu Phe Ser Leu Gln Leu Leu Leu Leu Asn Ala
    370                 375                 380
Asn Lys Ile Asn Ser Leu Arg Val Asp Ala Phe Gln Asp Leu His Asn
385                 390                 395                 400
Leu Asn Leu Leu Ser Leu Tyr Asp Asn Lys Leu Gln Thr Ile Ala Lys
                405                 410                 415
Gly Thr Phe Ser Pro Leu Arg Ala Ile Gln Thr Met His Leu Ala Gln
            420                 425                 430
Asn Pro Phe Ile Cys Asp Cys His Leu Lys Trp Leu Ala Asp Tyr Leu
        435                 440                 445
His Thr Asn Pro Ile Glu Thr Ser Gly Ala Arg Cys Thr Ser Pro Arg
    450                 455                 460
Arg Leu Ala Asn Lys Arg Ile Gly Gln Ile Lys Ser Lys Lys Phe Arg
465                 470                 475                 480
Cys Ser His His His His His His
                485

<210> SEQ ID NO 7
<211> LENGTH: 488
<212> TYPE: PRT
<213> ORGANISM: Artificial Sequence
<220> FEATURE:
<223> OTHER INFORMATION: SEQ ID NO:7 - Synthetic

<400> SEQUENCE: 7

Met Glu Thr Asp Thr Leu Leu Leu Trp Val Leu Leu Leu Trp Val Pro
1               5                   10                  15
Gly Ser Thr Gly Gly Gly Gly Ser Val Asp Asp Ile Gln Leu Thr
                20                  25                  30
Gln Ser Pro Ala Ile Met Ser Ala Ser Pro Gly Glu Lys Val Thr Met
            35                  40                  45
Thr Cys Arg Ala Ser Ser Ser Val Ser Tyr Met Asn Trp Tyr Gln Gln
        50                  55                  60
Lys Ser Gly Thr Ser Pro Lys Arg Trp Ile Tyr Asp Thr Ser Lys Val
65                  70                  75                  80
```

-continued

```
Ala Ser Gly Val Pro Tyr Arg Phe Ser Gly Ser Gly Thr Ser
                 85                  90                  95

Tyr Ser Leu Thr Ile Ser Ser Met Glu Ala Glu Asp Ala Ala Thr Tyr
            100                 105                 110

Tyr Cys Gln Gln Trp Ser Ser Asn Pro Leu Thr Phe Gly Ala Gly Thr
        115                 120                 125

Lys Leu Glu Leu Lys Gly Gly Ser Gly Gly Ser Gly Gly Ser Gly Gly
    130                 135                 140

Ser Gly Gly Asp Ile Lys Leu Gln Gln Ser Gly Ala Glu Leu Ala Arg
145                 150                 155                 160

Pro Gly Ala Ser Val Lys Met Ser Cys Lys Thr Ser Gly Tyr Thr Phe
                165                 170                 175

Thr Arg Tyr Thr Met His Trp Val Lys Gln Arg Pro Gly Gln Gly Leu
            180                 185                 190

Glu Trp Ile Gly Tyr Ile Asn Pro Ser Arg Gly Tyr Thr Asn Tyr Asn
        195                 200                 205

Gln Lys Phe Lys Asp Lys Ala Thr Leu Thr Thr Asp Lys Ser Ser Ser
    210                 215                 220

Thr Ala Tyr Met Gln Leu Ser Ser Leu Thr Ser Glu Asp Ser Ala Val
225                 230                 235                 240

Tyr Tyr Cys Ala Arg Tyr Tyr Asp Asp His Tyr Cys Leu Asp Tyr Trp
                245                 250                 255

Gly Gln Gly Thr Thr Leu Thr Val Ser Ser Val Glu Gly Gly Gly Gly
            260                 265                 270

Ser Leu His Cys Pro Ala Ala Cys Thr Cys Ser Asn Asn Ile Val Asp
        275                 280                 285

Cys Arg Gly Lys Gly Leu Thr Glu Ile Pro Thr Asn Leu Pro Glu Thr
    290                 295                 300

Ile Thr Glu Ile Arg Leu Glu Gln Asn Thr Ile Lys Val Ile Pro Pro
305                 310                 315                 320

Gly Ala Phe Ser Pro Tyr Lys Lys Leu Arg Arg Ile Asp Leu Ser Asn
                325                 330                 335

Asn Gln Ile Ser Glu Leu Ala Pro Asp Ala Phe Gln Gly Leu Arg Ser
            340                 345                 350

Leu Asn Ser Leu Val Leu Tyr Gly Asn Lys Ile Thr Glu Leu Pro Lys
        355                 360                 365

Ser Leu Phe Glu Gly Leu Phe Ser Leu Gln Leu Leu Leu Leu Asn Ala
    370                 375                 380

Asn Lys Ile Asn Ser Leu Arg Val Asp Ala Phe Gln Asp Leu His Asn
385                 390                 395                 400

Leu Asn Leu Leu Ser Leu Tyr Asp Asn Lys Leu Gln Thr Ile Ala Lys
                405                 410                 415

Gly Thr Phe Ser Pro Leu Arg Ala Ile Gln Thr Met His Leu Ala Gln
            420                 425                 430

Asn Pro Phe Ile Cys Asp Cys His Leu Lys Trp Leu Ala Asp Tyr Leu
        435                 440                 445

His Thr Asn Pro Ile Glu Thr Ser Gly Ala Arg Cys Thr Ser Pro Arg
    450                 455                 460

Arg Leu Ala Asn Lys Arg Ile Gly Gln Ile Lys Ser Lys Lys Phe Arg
465                 470                 475                 480

Cys Ser His His His His His
                485
```

```
<210> SEQ ID NO 8
<211> LENGTH: 488
<212> TYPE: PRT
<213> ORGANISM: Artificial Sequence
<220> FEATURE:
<223> OTHER INFORMATION: SEQ ID NO:8 - Synthetic

<400> SEQUENCE: 8

Met Glu Thr Asp Thr Leu Leu Leu Trp Val Leu Leu Trp Val Pro
1               5                   10                  15

Gly Ser Thr Gly Gly Gly Gly Ser Leu His Cys Pro Ala Ala Cys
                20                  25                  30

Thr Cys Ser Asn Asn Ile Val Asp Cys Arg Gly Lys Gly Leu Thr Glu
            35                  40                  45

Ile Pro Thr Asn Leu Pro Glu Thr Ile Thr Glu Ile Arg Leu Glu Gln
    50                  55                      60

Asn Thr Ile Lys Val Ile Pro Pro Gly Ala Phe Ser Pro Tyr Lys Lys
65                  70                  75                  80

Leu Arg Arg Ile Asp Leu Ser Asn Asn Gln Ile Ser Glu Leu Ala Pro
                85                  90                      95

Asp Ala Phe Gln Gly Leu Arg Ser Leu Asn Ser Leu Val Leu Tyr Gly
            100                 105                 110

Asn Lys Ile Thr Glu Leu Pro Lys Ser Leu Phe Glu Gly Leu Phe Ser
        115                 120                 125

Leu Gln Leu Leu Leu Leu Asn Ala Asn Lys Ile Asn Ser Leu Arg Val
    130                 135                 140

Asp Ala Phe Gln Asp Leu His Asn Leu Asn Leu Leu Ser Leu Tyr Asp
145                 150                 155                 160

Asn Lys Leu Gln Thr Ile Ala Lys Gly Thr Phe Ser Pro Leu Arg Ala
                165                 170                 175

Ile Gln Thr Met His Leu Ala Gln Asn Pro Phe Ile Cys Asp Cys His
            180                 185                 190

Leu Lys Trp Leu Ala Asp Tyr Leu His Thr Asn Pro Ile Glu Thr Ser
        195                 200                 205

Gly Ala Arg Cys Thr Ser Pro Arg Arg Leu Ala Asn Lys Arg Ile Gly
    210                 215                 220

Gln Ile Lys Ser Lys Lys Phe Arg Cys Ser Gly Gly Gly Ser Asp
225                 230                 235                 240

Ile Lys Leu Gln Gln Ser Gly Ala Glu Leu Ala Arg Pro Gly Ala Ser
                245                 250                 255

Val Lys Met Ser Cys Lys Thr Ser Gly Tyr Thr Phe Thr Arg Tyr Thr
            260                 265                 270

Met His Trp Val Lys Gln Arg Pro Gly Gln Gly Leu Glu Trp Ile Gly
        275                 280                 285

Tyr Ile Asn Pro Ser Arg Gly Tyr Thr Asn Tyr Asn Gln Lys Phe Lys
    290                 295                 300

Asp Lys Ala Thr Leu Thr Thr Asp Lys Ser Ser Ser Thr Ala Tyr Met
305                 310                 315                 320

Gln Leu Ser Ser Leu Thr Ser Glu Asp Ser Ala Val Tyr Tyr Cys Ala
                325                 330                 335

Arg Tyr Tyr Asp Asp His Tyr Cys Leu Asp Tyr Trp Gly Gln Gly Thr
            340                 345                 350

Thr Leu Thr Val Ser Ser Val Glu Gly Ser Gly Gly Ser Gly
        355                 360                 365

Ser Gly Gly Ser Gly Gly Val Asp Asp Ile Gln Leu Thr Gln Ser Pro
```

```
            370                 375                 380
Ala Ile Met Ser Ala Ser Pro Gly Glu Lys Val Thr Met Thr Cys Arg
385                 390                 395                 400

Ala Ser Ser Ser Val Ser Tyr Met Asn Trp Tyr Gln Gln Lys Ser Gly
                405                 410                 415

Thr Ser Pro Lys Arg Trp Ile Tyr Asp Thr Ser Lys Val Ala Ser Gly
                420                 425                 430

Val Pro Tyr Arg Phe Ser Gly Ser Gly Ser Gly Thr Ser Tyr Ser Leu
                435                 440                 445

Thr Ile Ser Ser Met Glu Ala Glu Asp Ala Ala Thr Tyr Tyr Cys Gln
                450                 455                 460

Gln Trp Ser Ser Asn Pro Leu Thr Phe Gly Ala Gly Thr Lys Leu Glu
465                 470                 475                 480

Leu Lys His His His His His His
                485

<210> SEQ ID NO 9
<211> LENGTH: 488
<212> TYPE: PRT
<213> ORGANISM: Artificial Sequence
<220> FEATURE:
<223> OTHER INFORMATION: SEQ ID NO:9 - Synthetic

<400> SEQUENCE: 9

Met Glu Thr Asp Thr Leu Leu Leu Trp Val Leu Leu Leu Trp Val Pro
1               5                   10                  15

Gly Ser Thr Gly Gly Gly Gly Ser Leu His Cys Pro Ala Ala Cys
                20                  25                  30

Thr Cys Ser Asn Asn Ile Val Asp Cys Arg Gly Lys Gly Leu Thr Glu
                35                  40                  45

Ile Pro Thr Asn Leu Pro Glu Thr Ile Thr Glu Ile Arg Leu Glu Gln
            50                  55                  60

Asn Thr Ile Lys Val Ile Pro Pro Gly Ala Phe Ser Pro Tyr Lys Lys
65                  70                  75                  80

Leu Arg Arg Ile Asp Leu Ser Asn Asn Gln Ile Ser Glu Leu Ala Pro
                85                  90                  95

Asp Ala Phe Gln Gly Leu Arg Ser Leu Asn Ser Leu Val Leu Tyr Gly
                100                 105                 110

Asn Lys Ile Thr Glu Leu Pro Lys Ser Leu Phe Glu Gly Leu Phe Ser
                115                 120                 125

Leu Gln Leu Leu Leu Leu Asn Ala Asn Lys Ile Asn Ser Leu Arg Val
            130                 135                 140

Asp Ala Phe Gln Asp Leu His Asn Leu Asn Leu Leu Ser Leu Tyr Asp
145                 150                 155                 160

Asn Lys Leu Gln Thr Ile Ala Lys Gly Thr Phe Ser Pro Leu Arg Ala
                165                 170                 175

Ile Gln Thr Met His Leu Ala Gln Asn Pro Phe Ile Cys Asp Cys His
                180                 185                 190

Leu Lys Trp Leu Ala Asp Tyr Leu His Thr Asn Pro Ile Glu Thr Ser
                195                 200                 205

Gly Ala Arg Cys Thr Ser Pro Arg Arg Leu Ala Asn Lys Arg Ile Gly
            210                 215                 220

Gln Ile Lys Ser Lys Lys Phe Arg Cys Ser Gly Gly Gly Gly Ser Val
225                 230                 235                 240

Asp Asp Ile Gln Leu Thr Gln Ser Pro Ala Ile Met Ser Ala Ser Pro
```

```
                 245                 250                 255
Gly Glu Lys Val Thr Met Thr Cys Arg Ala Ser Ser Val Ser Tyr
            260                 265                 270

Met Asn Trp Tyr Gln Gln Lys Ser Gly Thr Ser Pro Lys Arg Trp Ile
    275                 280                 285

Tyr Asp Thr Ser Lys Val Ala Ser Gly Val Pro Tyr Arg Phe Ser Gly
290                 295                 300

Ser Gly Ser Gly Thr Ser Tyr Ser Leu Thr Ile Ser Ser Met Glu Ala
305                 310                 315                 320

Glu Asp Ala Ala Thr Tyr Tyr Cys Gln Gln Trp Ser Ser Asn Pro Leu
                325                 330                 335

Thr Phe Gly Ala Gly Thr Lys Leu Glu Leu Lys Gly Gly Ser Gly Gly
            340                 345                 350

Ser Gly Gly Ser Gly Gly Ser Gly Gly Asp Ile Lys Leu Gln Gln Ser
        355                 360                 365

Gly Ala Glu Leu Ala Arg Pro Gly Ala Ser Val Lys Met Ser Cys Lys
370                 375                 380

Thr Ser Gly Tyr Thr Phe Thr Arg Tyr Thr Met His Trp Val Lys Gln
385                 390                 395                 400

Arg Pro Gly Gln Gly Leu Glu Trp Ile Gly Tyr Ile Asn Pro Ser Arg
                405                 410                 415

Gly Tyr Thr Asn Tyr Asn Gln Lys Phe Lys Asp Lys Ala Thr Leu Thr
            420                 425                 430

Thr Asp Lys Ser Ser Ser Thr Ala Tyr Met Gln Leu Ser Ser Leu Thr
        435                 440                 445

Ser Glu Asp Ser Ala Val Tyr Tyr Cys Ala Arg Tyr Tyr Asp Asp His
    450                 455                 460

Tyr Cys Leu Asp Tyr Trp Gly Gln Gly Thr Thr Leu Thr Val Ser Ser
465                 470                 475                 480

Val Glu His His His His His His
            485
```

<210> SEQ ID NO 10
<211> LENGTH: 1467
<212> TYPE: DNA
<213> ORGANISM: Artificial Sequence
<220> FEATURE:
<223> OTHER INFORMATION: SEQ ID NO:10 - Synthetic

<400> SEQUENCE: 10

```
atggagaccg acacactgct cctgtgggtc ctgctcctct gggtgccagg aagtacagga      60
ggaggaggag gaagcctgca ttgtccagca gcttgcacct gcagcaacaa catcgtggat     120
tgcagaggca agggcctgac agagatccct accaacctgc ccgagaccat caccgagatc    180
cggctggagc agaacaccat caaggtcatc cctcccggcg cctttagccc ttacaagaag    240
ctgcggcgga tcgacctgag caacaatcag atcagcgagc tggctccaga cgcctttcag    300
ggactgagaa gcctgaacag cctggtgctg tacggcaaca gatcaccga gctgcccaag    360
agcctgttcg agggactgtt cagcctgcag ctgctgctgc tgaacgccaa caagatcaac    420
agcctgagag tggacgcctt ccaggatctg acaacctga acctgctgag cctgtacgac    480
aacaagctgc agaccatcgc caagggcaca ttcagccccc tgagagccat ccagaccatg    540
cacctggccc agaacccctt catctgcgat tgccacctca gtggctggc cgattacctg    600
cacaccaatc tatcgagac cagcggagcc aggtgcacca gcctagaag actggccaac    660
```

```
aagcggatcg gccagatcaa gagcaagaag tttagatgca gcggcggagg cggaagcgat    720
atcaagctgc agcagagcgg cgcagaactg gctagaccag gcgccagcgt gaagatgtct    780
tgcaagacca gcggctacac cttcaccagg tacaccatgc attgggtgaa gcagagaccc    840
ggccagggac tcgagtggat cgggtacatt aacccagcc ggggctacac caactacaac    900
cagaagttca aggacaaggc caccctgacc accgacaagt ctagcagcac cgcctacatg    960
cagctgagct ctctgaccag cgaggatagc gccgtgtact attgcgcccg gtactacgac   1020
gaccactatt gcctggacta ttggggccag ggcacaacac tgaccgtgtc tagcgtggag   1080
ggaggaagcg gaggaagcgg aggaagcgga ggaagcggag gagtggacga tatccagctg   1140
acccagagcc cagctatcat gagcgcctct cccggcgaga aagtgaccat gacttgcagg   1200
gccagcagca gcgtgtccta catgaattgg taccagcaga agagcggcac cagcccaaag   1260
cgctggatct acgacaccag caaggtggca agcggcgtgc cttacagatt cagcggaagc   1320
ggcagcggca catcttacag cctgaccatc tctagcatgg aggccgaaga cgccgctaca   1380
tactactgcc agcagtggag cagcaacccc ctgacctttg gagccggaac caagctggag   1440
ctgaagcacc accaccatca ccactaa                                      1467
```